United States Patent
Kim et al.

(10) Patent No.: US 11,485,963 B2
(45) Date of Patent: Nov. 1, 2022

(54) D-PSICOSE 3-EPIMERASE AND METHOD FOR PRODUCING D-PSICOSE USING THE SAME

(71) Applicant: CJ CheilJedang Corporation, Seoul (KR)

(72) Inventors: Su Jin Kim, Seoul (KR); Young Mi Lee, Seoul (KR); Yang Hee Kim, Seoul (KR); Seong Bo Kim, Seoul (KR); Seung Won Park, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/763,041

(22) PCT Filed: Nov. 15, 2018

(86) PCT No.: PCT/KR2018/014038
§ 371 (c)(1),
(2) Date: May 11, 2020

(87) PCT Pub. No.: WO2019/098723
PCT Pub. Date: May 23, 2019

(65) Prior Publication Data
US 2021/0261939 A1    Aug. 26, 2021

(30) Foreign Application Priority Data

Nov. 15, 2017  (KR) .......................... 10-2017-0152619

(51) Int. Cl.
*C12N 9/90*    (2006.01)
*C12P 19/02*   (2006.01)
*C12P 19/24*   (2006.01)

(52) U.S. Cl.
CPC ................ *C12N 9/90* (2013.01); *C12P 19/02* (2013.01); *C12P 19/24* (2013.01); *C12Y 501/03* (2013.01)

(58) Field of Classification Search
CPC ................................. C12N 9/90; C12P 19/02
See application file for complete search history.

(56) References Cited

U.S. PATENT DOCUMENTS

| 8,008,058 | B2 |   | 8/2011  | Maruta et al. |          |
|-----------|----|---|---------|---------------|----------|
| 9,988,618 | B2 | * | 6/2018  | Kim ........... | C12Y 501/03 |
| 10,550,414| B2 | * | 2/2020  | Kim ........... | C12N 1/205 |
| 11,174,475| B2 | * | 11/2021 | Kim ........... | C12Y 501/03 |

FOREIGN PATENT DOCUMENTS

| KR | 10-2011-0035805 A | 4/2011 |
| KR | 10-1318422 B1     | 10/2013 |
| KR | 10-2014-0140215 A | 12/2014 |

(Continued)

OTHER PUBLICATIONS

International Search Report issued in corresponding International Patent Application No. PCT/KR2018/014038 dated Mar. 7, 2019.

(Continued)

*Primary Examiner* — Yong D Pak
(74) *Attorney, Agent, or Firm* — Morgan, Lewis & Bockius LLP

(57) ABSTRACT

The present disclosure relates to novel D-psicose 3-epimerase and a method for producing psicose using the same.

17 Claims, 4 Drawing Sheets

Specification includes a Sequence Listing.

(56) References Cited

FOREIGN PATENT DOCUMENTS

| KR | 10-1473918 B1 | 12/2014 | | |
|---|---|---|---|---|
| KR | 10-1539096 B1 | 7/2015 | | |
| KR | 10-1539097 B1 | 7/2015 | | |
| KR | 10-2017-0075672 A | 7/2017 | | |
| WO | WO-2015/182937 A1 * | 12/2015 | ............. | C12P 19/24 |
| WO | WO-2017/111563 A1 * | 6/2017 | ............. | C12N 1/205 |

OTHER PUBLICATIONS

CBI, GenBank accession No. WP_029076714.1 dated Jun. 13, 2014.
Bilik et al., Reaction of saccharides catalyzed by molybdate ions. IX. Epimerization of ketohexoses. Chem Zvesti 28:106-109 (1973).
Doner, "Isomerization of d-fructose by base: liquid-chromatographic evaluation and the isolation of d-psicose," Carbohydrate Research, 70:209-216 (1979).
Kim et al., "Characterization of an Agrobacterium tumefaciens D-psicose 3-epimerase that converts D-fructose to D-psicose," Applied Environmental Microbiology, 72(2):981-985 (2006).

\* cited by examiner

[Fig. 1]
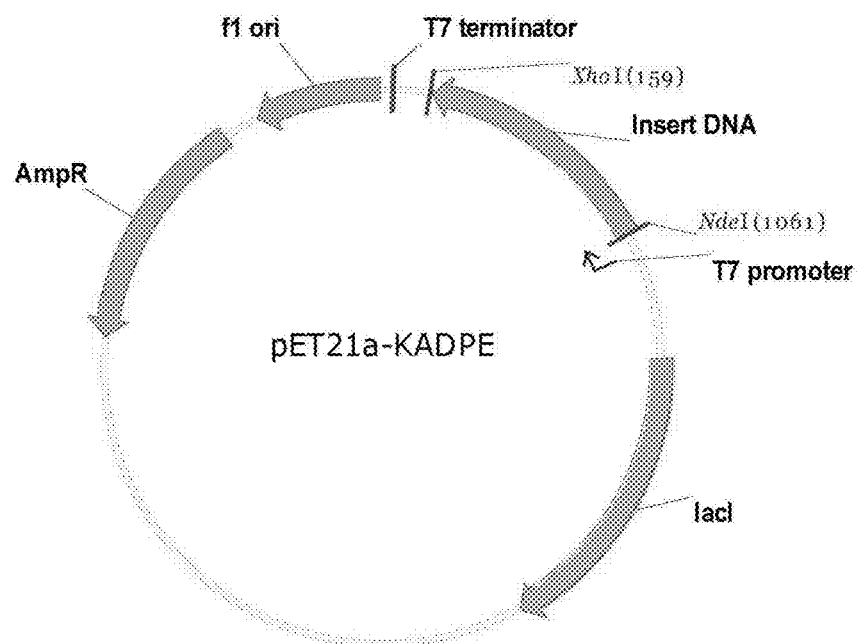

[Fig. 2]
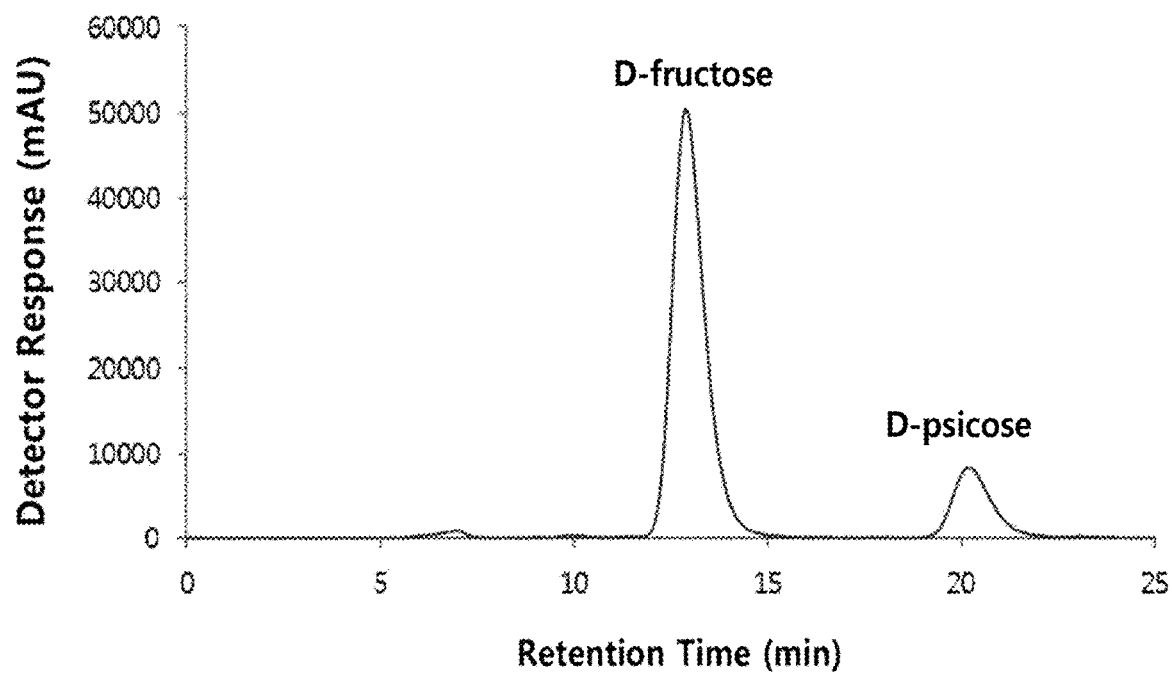

[Fig. 3a]
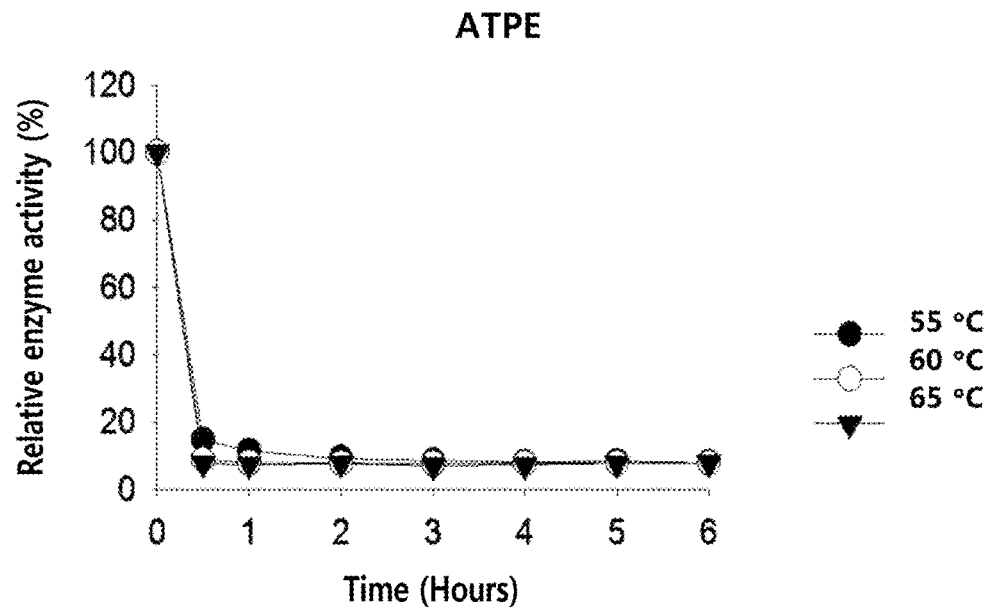
[Fig. 3b]
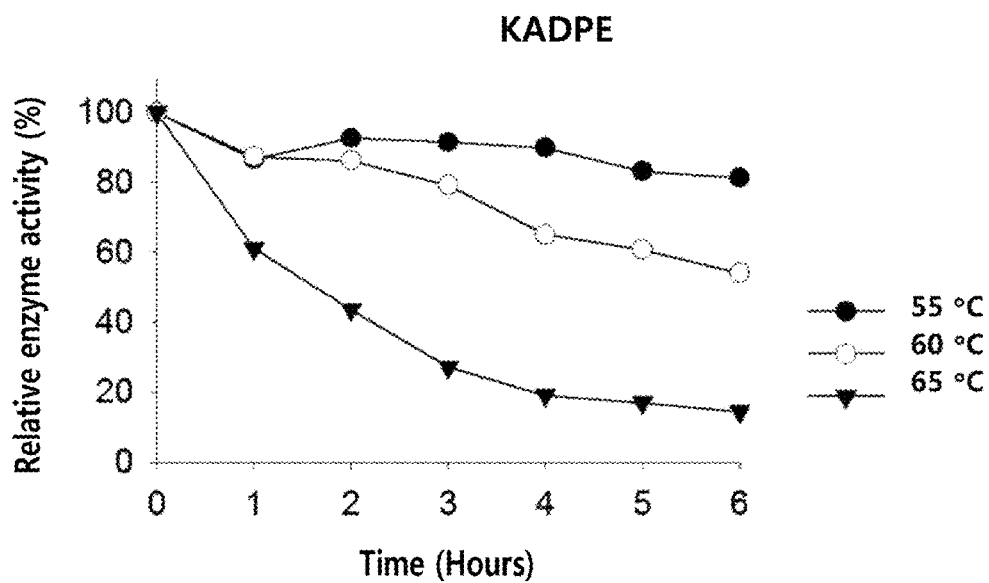

[Fig. 4]
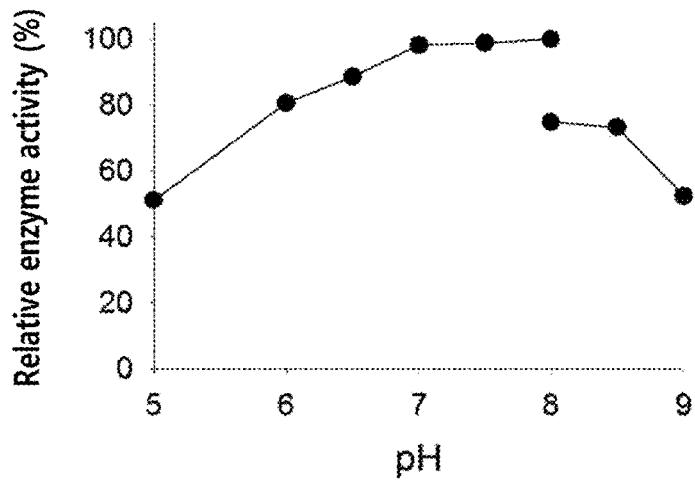
[Fig. 5]
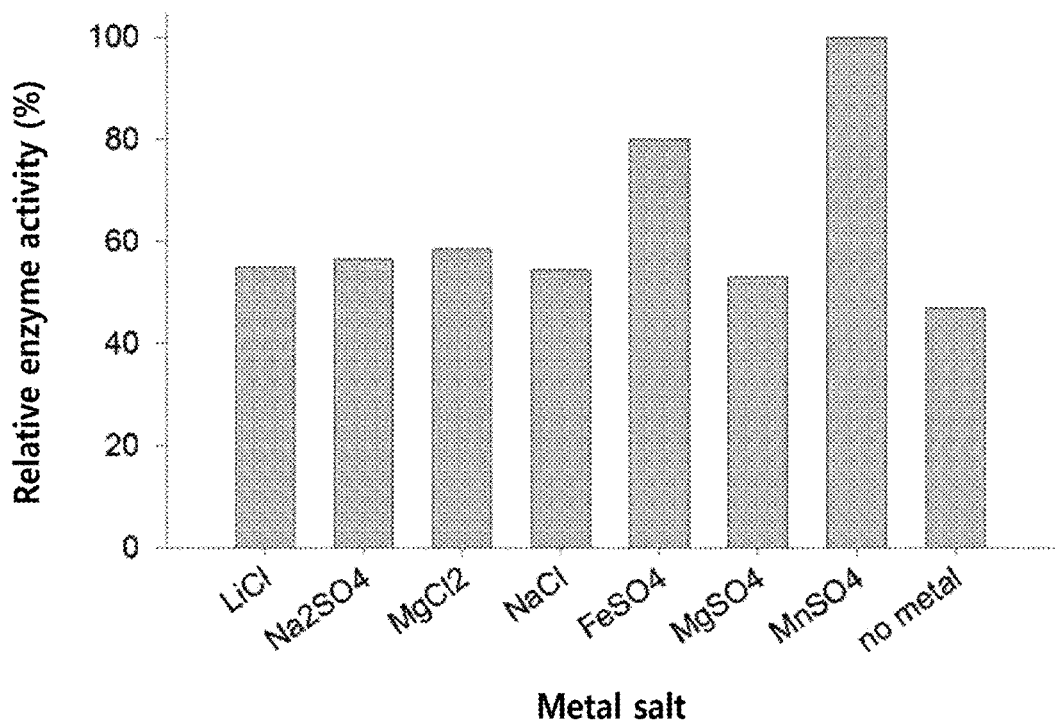

D-PSICOSE 3-EPIMERASE AND METHOD FOR PRODUCING D-PSICOSE USING THE SAME

SEQUENCE LISTING SUBMISSION VIA EFS-WEB

A computer readable text file, entitled "SequenceListing.txt," created on or about Sep. 10, 2020 with a file size of about 7 kb contains the sequence listing for this application and is hereby incorporated by reference in its entirety.

TECHNICAL FIELD

The present disclosure relates to D-psicose 3-epimerase and a method for producing D-psicose using the same.

BACKGROUND ART

D-Psicose (hereinafter referred to as "psicose") is a monosaccharide known as a rare sugar present in nature. Psicose has a sweetness degree of about 70%, has nearly zero calories, and has received much attraction as a novel food ingredient due to its functionalities such as inhibition of blood glucose, inhibition of fat synthesis, etc.

Due to these features, psicose is being considered for use as a sweetener that can replace sugar used in various foods. However, since there are only trace amounts of psicose in nature, there is an increased need for the development of a method to efficiently produce psicose.

A method using the catalysis of molybdate ions (Bilik V, Tihlarik K, 1973, Reaction of saccharides catalyzed by molybdate ions. IX. Epimerization of ketohexoses. Chem Zvesti 28:106-109), a chemical method for producing psicose from D-fructose by heating with ethanol and triethylamine (Doner L W, 1979, Isomerization of d-fructose by base: liquid-chromatographic evaluation and the isolation of d-psicose. Carbohydr Res. 70:209-216), and a biological method for producing psicose from D-fructose by using a microorganism producing D-psicose 3-epimerase (Korean Patent Publication Application No. 10-2011-0035805) are known as methods for producing psicose, and are conventionally known in the art. However, these methods are disadvantageous in that the production of psicose by chemical methods requires a complicated purification process due to the large amount of byproducts generated, and in that the biological method has a very low yield and requires high production costs.

PRIOR-ART DOCUMENT

Patent Document

Patent Document 1: Korean Patent No. 10-1318422
Patent Document 2: Korean Patent Publication Application No. 10-2011-0035805

Non-Patent Document

Non-patent Document 1: Bilik V, Tihlarik K, 1973, Reaction of saccharides catalyzed by molybdate ions. IX. Epimerization of ketohexoses. Chem Zvesti 28:106-109
Non-patent Document 2: Doner L W, 1979, Isomerization of d-fructose by base: liquid-chromatographic evaluation and the isolation of d-psicose. Carbohydr Res. 70:209-216
Non-patent Document 3: Kim H J, Hyun E K, Kim Y S, Lee Y J, Oh D K, 2006, Characterization of an Agrobacterium tumefaciens D-psicose 3-epimerase that converts D-fructose to D-psicose. Appl Environ Microbiol. 72(2): 981-5

DISCLOSURE

Technical Problem

The present inventors have made extensive efforts to develop a method capable of improving the production yield of psicose. As a result, they have completed the present disclosure by discovering that the conversion rate from D-fructose to psicose can be increased when using the novel D-psicose 3-epimerase (hereinafter referred to as "psicose epimerase") of the present disclosure, thereby remarkably improving the production yield of psicose.

Technical Solution

An object of the present disclosure is to provide novel psicose epimerase, a polynucleotide encoding the enzyme, a recombinant vector comprising the polynucleotide, and a microorganism into which the vector is introduced.

Another object of the present disclosure is to provide a composition for producing D-psicose, which comprises the psicose epimerase of the present disclosure, a microorganism expressing the enzyme, or a culture of the microorganism; and a method for producing D-psicose using the enzyme.

Advantageous Effects

The psicose epimerase of the present disclosure has an excellent activity of converting D-fructose to psicose, possesses high-temperature stability which enables industrial application thereof, and has an effect wherein the rate of the conversion reaction is rapid. Therefore, it is advantageous in that when the enzyme of the present disclosure is used to produce psicose, the psicose can be produced with high efficiency and high yield.

BRIEF DESCRIPTION OF DRAWINGS

FIG. 1 is a diagram of a recombinant vector for expressing psicose epimerase (KADPE) consisting of an amino acid sequence of SEQ ID NO: 1.

FIG. 2 is a graph showing analysis data of HPLC on the results of the production of psicose using the KADPE of the present disclosure and D-fructose as a substrate.

FIG. 3 is graphs showing the relative enzyme activities of psicose epimerase according to temperatures. FIG. 3a shows the activity of conventional D-psicose 3-epimerase (ATPE) derived from Agrobacterium tumefaciens; and FIG. 3b shows the activity of the KADPE of the present disclosure.

FIG. 4 is a graph showing the relative psicose epimerase activity of the KADPE of the present disclosure according to the pH change.

FIG. 5 is a graph showing the relative psicose epimerase activity of the KADPE of the present disclosure according to the metal addition.

BEST MODE

An aspect of the present disclosure provides psicose epimerase consisting of an amino acid sequence of SEQ ID NO: 1.

In an exemplary embodiment, the psicose epimerase of the present disclosure may comprise a polypeptide having a homology to the amino acid sequence of SEQ ID NO: 1 of at least 80%, 90%, 95%, 97%, or 99%. It is apparent that a protein having an amino acid sequence having substitution, insertion, modification, and/or deletion of some amino acid sequences of SEQ ID NO: 1 falls within the scope of the present disclosure as long as it is the amino acid sequence having the homology above and the activity of converting D-fructose to psicose. Additionally, for the polypeptide having the activity of psicose epimerase, any polypeptide encoded by a polynucleotide which is hybridized under stringent conditions with probe(s) that can be prepared from known gene sequences, for example, complementary sequence(s) to all or part of the above nucleotide sequence encoding the psicose epimerase of the present disclosure, can be included without limitation.

As used herein, the term "polynucleotide" refers to a polyribonucleotide or a deoxyribonucleotide which is unmodified or modified with a nucleotide polymer composed of nucleotide monomers covalently bonded in a long chain.

As used herein, the term "stringent conditions" refers to conditions that are designed to permit specific hybridization between polynucleotides. Such conditions rely on the length and degree of complementarity of the polynucleotides, and the related parameters are well known in the art, and are specifically described in references (e.g., J. Sambrook et al., supra). For example, the stringent conditions may include a condition in which genes having a high homology (i.e., 80% or more, 90% or more, 95% or more, 97% or more, or 99% or more) can hybridize between them, whereas genes having a lower homology thereof cannot hybridize with each other; or conditions for conventional southern hybridization (i.e., conditions for washing once, and specifically two or three times under a salt concentration and temperature corresponding to 60° C., 1×SSC, 0.1% SDS; specifically under 60° C., 0.1×SSC, 0.1% SDS, and more specifically under 68° C., 0.1×SSC, 0.1% SDS). The probe used for the hybridization may be a part of the nucleotide sequence complementary to the above nucleotide sequences. Such probe can be prepared by PCR using an oligonucleotide prepared based on a known sequence as a primer and a gene fragment containing such nucleotide sequence as a template. Additionally, those skilled in the art can adjust the temperature and the salt concentration in the washing solution as needed depending on the factor such as the length of the probe.

As used herein, the term "homology" refers to the percentage of identity between two polynucleotide or polypeptide moieties. The homology between sequences from a moiety to another moiety may be determined by a technique known in the art. For example, the homology may be determined by directly arranging the sequence information, i.e., parameters such as score, identity, similarity, etc., of two polynucleotide molecules or two polypeptide molecules using an easily accessible computer program (Example: BLAST 2.0). Additionally, the homology between polynucleotides may be determined by hybridizing polynucleotides under the condition of forming a stable double-strand between the homologous regions, disassembling with a single strand-specific nuclease, followed by size determination of the disassembled fragments.

Additionally, as long as a protein has efficacy corresponding to that of the psicose epimerase of the present disclosure, which consists of the amino acid sequence of SEQ ID NO: 1, it does not exclude a mutation that can occur by a meaningless sequence addition upstream or downstream of the amino acid sequence of SEQ ID NO: 1, a naturally occurring mutation, or a silent mutation. In addition, a protein including the amino acid sequence of SEQ ID NO: 1 also belongs to the scope of the present disclosure.

Further, the D-psicose 3-epimerase of the present disclosure may be encoded by the nucleotide sequence of SEQ ID NO: 2, or the D-psicose 3-epimerase may be encoded by a nucleotide sequence having a homology to the nucleotide sequence of SEQ ID NO: 2 of at least 80%, 90%, 95%, 97%, or 99%, but is not limited thereto. In addition, based on codon degeneracy, it is apparent that proteins which consist of the amino acid sequence of SEQ ID NO: 1, or polynucleotides which can be translated into proteins having a homology to the above proteins, can also be included in the scope of the sequences of the polynucleotide which encode the D-psicose 3-epimerase of the present disclosure. Those skilled in the art will understand that based on a gene recombinant technique known in the art, the polynucleotide encoding the enzymes having substantially equivalent activities can be prepared by substituting, adding, and/or deleting one or more nucleotide sequences of SEQ ID NO: 2.

In another exemplary embodiment, the psicose epimerase of the present disclosure may be derived from a microorganism of the genus *Kaistia*. Specifically, the psicose epimerase of the present disclosure may be derived from *Kaistia adipata*, and more specifically it may be derived from *Kaistia adipata* KCTC 12095.

In still another exemplary embodiment, the psicose epimerase of the present disclosure may have a molecular weight of 25 kDa to 37 kDa, 27 kDa to 35 kDa, or 30 kDa to 35 kDa, which is measured by sodium dodecyl sulfate polyacrylamide gel electrophoresis (SDS-PAGE).

Another aspect of the present disclosure provides a polynucleotide encoding psicose epimerase consisting of an amino acid sequence of SEQ ID NO: 1.

In an exemplary embodiment, the polynucleotide provided in the present disclosure may be a polynucleotide consisting of the nucleotide sequence of SEQ ID NO: 2, or a polynucleotide consisting of a sequence having a homology to the nucleotide sequence of SEQ ID NO: 2 of 80% or more, 90% or more, 95% or more, 97% or more, or 99% or more. In addition, based on codon degeneracy, for the polynucleotide provided in the present disclosure, it is apparent that proteins which consist of the amino acid sequence of SEQ ID NO: 1, or polynucleotides which can be translated into proteins having a homology to the proteins consisting of the amino acid sequence of SEQ ID NO: 1, can also be included in the scope of the present disclosure.

Still another aspect of the present disclosure provides a recombinant vector comprising the polynucleotide encoding the D-psicose 3-epimerase of the present disclosure.

The recombinant vector of the present disclosure may be in the form in which the polynucleotide encoding the psicose epimerase is inserted into a cloning vector or expression vector by using a known standard method. In the present disclosure, the "cloning vector" refers to a vector capable of carrying a DNA fragment into a host cell and reproducing the same. The cloning vector may further comprise a polyadenylation signal, a transcription termination sequence, and/or a multiple cloning site. Herein, the multiple cloning site may comprise at least one of an endonuclease and a restriction enzyme site. For example, the polynucleotide encoding the psicose epimerase may be located upstream of the polyadenylation signal and the transcription termination sequence. In the present disclosure, the "expression vector"

refers to a DNA sequence necessary for transcription and translation of DNA cloned in a suitable host. Additionally, in the present disclosure, the "expression vector" refers to a gene construct comprising an essential regulatory element operably linked to an insert such that the insert is expressed when present in cells of the subject. The "operably linked" refers to a linkage wherein one or more functions are regulated by another due to polynucleotide sequence correlation on the polynucleotide. The expression vector may be prepared and purified using a standard recombinant DNA technique. The expression vector may include one or more of a promoter, an initiation codon, a gene encoding the psicose epimerase, and a termination codon.

Still another aspect of the present disclosure provides a microorganism into which the recombinant vector of the present disclosure is introduced.

In an specific exemplary embodiment, the microorganism into which the recombinant vector of the present disclosure is introduced may be one transformed by a recombinant vector including the polynucleotide encoding psicose epimerase consisting of the amino acid sequence of SEQ ID NO: 1, or one transformed by a recombinant vector including the polynucleotide consisting of the nucleotide sequence of SEQ ID NO: 2.

As used herein, the term "transformation" means that a gene or a recombinant vector including the gene is introduced into a host cell so that it can be expressed in the host cell. The transformed gene can be located anywhere without limitation, whether it is inserted in the chromosome of a host cell or located outside the chromosome, as long as it can be expressed in the host cell. The transformation method of the present disclosure may include transient transformation microinjection, transduction, cell fusion, calcium phosphate precipitation, liposome-mediated transfection, DEAE dextran-mediated transfection, electroporation, electroinjection, chemical treatment, etc., but is not limited thereto. The host cell which can be transformed into the recombinant vector may include a prokaryotic cell, a plant cell, an animal cell, etc., but the host cell having high DNA introduction efficiency and a high expression rate of introduced DNA can be used. For example, the host cell may include *E. coli*, a strain of the genus *Bacillus*, a strain of the genus *Corynebacterium*, a strain of the genus *Salmonella*, etc. For example, the host cell may include *E. coli* such as W3110, BL21, JM109, K-12, LE392, RR1, and DH5. More specifically, the microorganism of the present disclosure may be *E. coli* BL21 (DE3)/KADPE, which is deposited as KCCM11918P.

Still another aspect of the present disclosure provides a composition for producing D-psicose, which comprises psicose epimerase consisting of an amino acid sequence of SEQ ID NO: 1, a microorganism expressing the psicose epimerase, or a culture of the microorganism.

In a specific exemplary embodiment, the microorganism of the present disclosure may be a strain itself, a culture of the strain, or a lysate of the microorganism. The culture or lysate of the present disclosure may include the D-psicose 3-epimerase of the present disclosure. In addition, the culture of the microorganism of the present disclosure may or may not include the above microorganism. Further, the lysate of the microorganism of the present disclosure may be a lysate obtained by disrupting the microorganism or a culture thereof, or a supernatant obtained by centrifuging the lysate.

In another specific exemplary embodiment, the composition of the present disclosure for producing D-psicose may further comprise D-fructose, which is used as a substrate for psicose epimerase.

In still another specific exemplary embodiment, the microorganism of the present disclosure may be used by immobilizing on a carrier. An Example of the carrier that can be used in the present disclosure includes agar, agarose, k-carrageenan, alginate, or chitosan, but is not limited thereto.

Additionally, the composition of the present disclosure for producing D-psicose may further include any ingredient capable of assisting the production of psicose. Specifically, the composition of the present disclosure for producing D-psicose may further include a metal. More specifically, the metal of the present disclosure may be one or more metals selected from the group consisting of manganese, magnesium, iron, lithium, and sodium. In addition, the metal of the present disclosure may be a metal ion or a metal salt. The metal of the present disclosure (e.g., specifically, the metal ion or metal salt) may be used in an amount of 0.1 mM to 10 mM, 0.1 mM to 7 mM, 0.1 mM to 4 mM, 0.5 mM to 10 mM, 0.5 mM to 7 mM, 0.5 mM to 4 mM, 1 mM to 10 mM, 1 mM to 7 mM, 1 mM to 4 mM, 2 mM to 10 mM, 2 mM to 7 mM, or 2 mM to 4 mM. More specifically, the metal salt of the present disclosure may be one or more metal salts selected from the group consisting of $LiCl$, $Na_2SO_4$, $MgCl_2$, $NaCl$, $FeSO_4$, $MgSO_4$, $MnCl_2$, and $MnSO_4$.

Still another aspect of the present disclosure provides a method for producing D-psicose, comprising reacting D-fructose with psicose epimerase consisting of an amino acid sequence of SEQ ID NO: 1, a microorganism expressing the psicose epimerase of the present disclosure, or a culture of the microorganism.

In a specific exemplary embodiment, the production method of the present disclosure may further comprise adding a metal before, after, or simultaneously with reacting the D-fructose of the present disclosure.

In another specific exemplary embodiment, the production method of the present disclosure may further comprise isolating and/or purifying a reaction resultant including psicose, after reacting the D-fructose of the present disclosure or adding the metal of the present disclosure. The isolation and/or purification may be performed by one or more known methods such as dialysis, precipitation, adsorption, electrophoresis, ion exchange chromatography, and fractional crystallization, but these are not limited thereto.

Additionally, the production method of the present disclosure may further comprise carrying out decolorization and/or desalinization before or after each of the isolation step and/or purification step of the present disclosure. By carrying out the decolorization and/or desalinization, more purified psicose can be obtained without impurities.

In still another specific embodiment, the production method of the present disclosure may further comprise crystallizing D-psicose after reacting the D-fructose of the present disclosure, adding a metal, isolation and/or purification, or decolorization and/or desalinization. The crystallization can be carried out using a crystallization method conventionally used in the art. For example, the crystallization can be carried out using a cooling crystallization method.

In still another specific embodiment, the production method of the present disclosure may further comprise concentrating psicose before carrying out the crystallization step of the present disclosure. The concentration may increase the crystallization efficiency.

In still another specific embodiment, the production method of the present disclosure may further comprise reacting the unreacted D-fructose with psicose epimerase after the isolation step and/or purification step of the present disclosure; reusing a mother liquid from which the crystals are isolated in the isolation step and/or purification step after the crystallization step of the present disclosure; or a combination thereof. Through the additional steps, psicose can be obtained at a higher yield, and the amount of discarded D-fructose can be reduced, which is economically advantageous.

In still another specific embodiment, the reaction of the present disclosure may be carried out at a pH of 5.0 to 9.0, a temperature of 40° C. to 90° C., and/or for 0.5 hours to 48 hours.

Specifically, the reaction of the present disclosure may be carried out at a pH of 6.0 to 8.5, a pH of 6.0 to 8.0, or a pH of 7.0 to 8.0.

Additionally, the reaction of the present disclosure may be carried out at a temperature of 40° C. to 80° C., 40° C. to 75° C., 40° C. to 65° C., 50° C. to 90° C., 50° C. to 80° C., 50° C. to 75° C., 50° C. to 65° C., 55° C. to 90° C., 55° C. to 80° C., 55° C. to 75° C., 55° C. to 65° C., 60° C. to 90° C., 60° C. to 80° C., 60° C. to 75° C., 60° C. to 65° C., 65° C. to 90° C., 65° C. to 80° C., or 65° C. to 75° C.

Further, the reaction of the present disclosure may be carried out for 0.5 hours or more, 1 hour or more, 3 hours or more, 5 hours or more, or 6 hours or more, and/or 48 hours or less, 36 hours of less, 24 hours or less, 12 hours or less, or 9 hours or less.

The psicose epimerase, metal, and carrier described in the method of the present disclosure for producing D-psicose are as described above.

Still another aspect of the present disclosure provides a use of the psicose epimerase of the present disclosure, a microorganism expressing the enzyme, or a culture of the microorganism in the production of psicose.

MODE FOR INVENTION

Hereinbelow, the present disclosure will be described in detail with accompanying exemplary embodiments. It should be understood, however, that the present disclosure is not limited to the embodiments below, and that various modifications and changes may be made by those skilled in the art within the spirit and scope of the present disclosure.

Throughout the specification of the present disclosure, the symbol "%" used to denote the concentration of a specific substance indicates that solid/solid is (weight/weight) %, solid/liquid is (weight/volume) %, and that liquid/liquid is (volume/volume) % unless otherwise stated.

EXAMPLES

Example 1

Preparation of Transformant Strain Producing Psicose Epimerase Derived from Strain of the Genus *Kaistia*

A recombinant expression vector and transformed microorganism containing a gene having the activity of psicose epimerase for converting D-fructose to psicose from a microorganism of the genus *Kaistia* were prepared.

Specifically, based on the gene sequences of the microorganism of the genus *Kaistia* registered in Genbank, the gene was cloned by PCR. Thereafter, based on the information of the amino acid sequence (SEQ ID NO: 1) and nucleotide sequence (SEQ ID NO: 2) of the gene, a forward primer (SEQ ID NO: 3) and a reverse primer (SEQ ID NO: 4) were devised and synthesized. Polymerase chain reaction (PCR) was carried out to amplify the gene with the synthesized primers using *Kaistia adipata* KCTC 12095 genomic DNA as a template. Specifically, PCR was carried out for a total of 33 cycles under the following conditions: denaturation at 94° C. for 1 minute, annealing at 58° C. for 30 seconds, and polymerization at 72° C. for 1 minute. The amplified gene was purified using a PCR purification kit (Quiagen Inc.), and then inserted into pET21a(+) (Novagen Inc., U.S.A.) using restriction enzymes NdeI and xhoI to prepare a recombinant vector, pET21a(+)-KADPE (FIG. 1).

The recombinant vector was transformed into *E. coli* BL21(DE3) by heat shock transformation (Sambrook and Russell: Molecular cloning, 2001), and then stored frozen in 50% glycerol for use. The transformant strain was named as *E. coli* BL21(DE3)/KADPE, and deposited to the Korean Culture of Microorganisms (KCCM), which is an international depositary authority under the Budapest Treaty, on Oct. 20, 2016, and assigned Accession No. KCCM11917P.

Example 2

Production and Purification of Psicose Epimerase

In order to produce psicose epimerase from the *E. coli* BL21(DE3)/KADPE prepared in Example 1, the *E. coli* BL21(DE3)/KADPE was inoculated into 5 mL of LB-ampicillin medium (Difco™), and then cultured with shaking at 37° C. at 200 rpm until the absorbance measured at 600 nm reached 1.5. Thereafter, the shake-cultured solution was inoculated into 500 mL of LB-ampicillin medium, 0.5 mM isopropyl β-D-1-thiogalactopyranoside (IPTG) was added thereto when the absorbance at 600 nm reached 0.7, and then the main culture was carried out at 16° C. at 150 rpm for 16 hours.

The main cultured solution was centrifuged at 8000 rpm for 20 minutes to recover only the cells; washed twice with 0.85% (w/v) NaCl; lysed in a lysis buffer (50 mM Tris-HCl, 300 mM NaCl, pH 7.0); and then disrupted using an ultrasonic processor at 4° C. for 20 minutes. The lysate was centrifuged at 4° C. at 13,000 rpm for 20 minutes to recover a supernatant, and the supernatant was applied to a Ni-NTA column (Ni-NTA Superflow, Qiagen Inc.) previously equilibrated with the lysis buffer. Thereafter, a lysis buffer (50 mM Tris-HCl, 300 mM NaCl, pH 7.0) containing 250 mM imidazole was sequentially flowed therein, and then purified psicose epimerase (hereinafter referred to as "KADPE") was obtained. As a result of SDS-PAGE, the KADPE was found to have a monomer having a size of about 32 kDa.

Example 3

Confirmation of KADPE Activity

Example 3-1: Confirmation of Conversion Activity from D-Fructose to Psicose

In order to confirm whether the KADPE produces psicose using D-fructose as a substrate, the KADPE (50 mM Tris-HCl, pH 7.0) produced in Example 2 was added to a 50 mM Tris-HCl buffer (pH 8.0) containing 50% D-fructose and 3 mM MnSO$_4$, and the reaction was carried out at 55° C. for 6 hours. Thereafter, the reaction was stopped by heating the reactant at 100° C. for 5 minutes, and then the production of psicose was confirmed by HPLC analysis. The HPLC analysis was carried out using a Refractive Index Detector (Agilent 1260 RID) of HPLC (Agilent Inc., U.S.A.) equipped with an Aminex HPX-87C column (BIO-RAD Inc.); in the HPLC analysis, the mobile phase solvent was water, the temperature was 80° C., and the flow rate was 0.6 mL/min.

As a result, it was confirmed that the KADPE produced psicose from D-fructose (FIG. 2).

Example 3-2

Confirmation of Conversion Rate from D-Fructose to Psicose

In order to confirm whether the psicose-producing ability of the KADPE is superior to that of psicose epimerase (ATPE, SEQ ID NO: 5, Korean Patent Laid-open No. 10-2011-0035805), which is used in the conventional production of psicose, the conversion rate from D-fructose to psicose was confirmed.

Specifically, the *E. coli* BL21(DE3) from which the recombinant expression vector pET24a-ATPE had been transformed was inoculated into LB medium containing kanamycin at a concentration of 10 μg/mL, and then the enzyme was expressed and purified in the same manner as in Example 2. The obtained enzyme was added to a 50 mM Tris-HCl buffer (pH 8.0) containing D-fructose (50 wt %) and 3 mM MnSO$_4$, and the reaction was carried out at 55° C. for 6 hours. Thereafter, the reaction was stopped by heating the reactant at 100° C. for 5 minutes, and then the production of psicose was confirmed by HPLC analysis. The HPLC analysis was carried out under the same conditions as in Example 3-1.

The conversion rate to psicose was calculated as the amount of psicose (mg/minute), in which the enzymes are produced per minute. The reaction rate of the KADPE was shown as a relative value while using the reaction rate of the ATPE as 100%.

As a result, the amount of psicose produced per minute when using the KADPE was 146.6% compared to the amount of psicose produced when using the ATPE, and thus it was confirmed that the conversion rate from D-fructose to psicose was remarkably high when using the KADPE (Table 1).

TABLE 1

| Enzyme | KADPE | ATPE |
|---|---|---|
| Relative reaction rate (%) | 146.6 | 100 |

Example 4

Analysis of Properties of KADPE 4-1. Analysis of Enzyme Activity According to Temperature The KADPE and D-fructose substrate were reacted for 2 hours at various temperatures (i.e., 40° C., 45° C., 50° C., 55° C., 60° C., 65° C., 70° C., and 75° C.), and then the enzyme activities at the different temperatures were compared. The reaction was carried out in the same manner as in Example 3-1 except for the temperature and reaction time. The enzyme activity was measured as the conversion rate from D-fructose to psicose.

As a result, it was confirmed that the KADPE showed a 25% or higher conversion activity at all of the temperature ranges, and that the activity of the KADPE was increased as the temperatures increased, which exhibited the maximum conversion rate at the highest temperature (i.e., 75° C.) (Table 2).

TABLE 2

| Temperature(° C.) | KADPE (Conversion rate, %) |
|---|---|
| 40 | 27.6 |
| 45 | 28.2 |
| 50 | 29.4 |
| 55 | 29.7 |
| 60 | 30.7 |
| 65 | 30.7 |
| 70 | 31.0 |
| 75 | 32.8 |

4-2. Analysis of Thermal Stability of Enzyme

In order to compare the thermal stability of the KADPE with that of the ATPE, which is a conventional enzyme, each of the enzymes was heat-treated at various temperatures (55° C., 60° C., and 65° C.), and then the enzyme treatment solution was sampled at different heat-treatment times (0.5 hours, 1 hour, 2 hours, 3 hours, 4 hours, 5 hours, and 6 hours) to measure the residual activity of each enzyme. The reaction was carried out for 30 minutes using the same method as in Example 3-1 except for the reaction times, and the residual activities of the enzymes were measured as the conversion rate from D-fructose to psicose.

As a result, it was confirmed that the KADPE had a high thermal stability because the decrease in half-life of the KADPE according to the increase in temperature was remarkably smaller than that of the ATPE (FIGS. 3a and 3b).

Example 4-3

Analysis of Enzyme Activity According to pH

In order to measure the enzyme activity according to pH, the D-fructose substrate was reacted with the KADPE at various pHs. Herein, the reaction was carried out in the same manner as in Example 3-1 except for the reaction time and pH.

Specifically, the enzymatic reaction was carried out at 55° C. for 30 minutes by using 50 mM potassium phosphate at pH 5.0, pH 6.0, pH 6.5, pH 7.0, pH 7.5, and pH 8.0; and by using a 50 mM Tris-HCl buffer at pH 8.0, pH 8.5, and pH 9.0. Thereafter, the enzyme activity was measured as the conversion rate from D-fructose to psicose.

As a result, it was confirmed that the KADPE showed a 70% or higher activity at pH 6 to pH 8.5 relative the maximum activity, and showed the highest activity at pH 8.0 (Table 3, FIG. 4).

TABLE 3

| | pH | Relative conversion rate (%) |
|---|---|---|
| 50 mM Potassium phosphate | 5 | 51 |
| | 6 | 81 |
| | 6.5 | 89 |
| | 7 | 98 |
| | 7.5 | 99 |
| | 8 | 100 |
| 50 mM Tris-HCl | 8 | 75 |
| | 8.5 | 73 |
| | 9 | 52 |

4-4. Analysis of Enzyme Activity According to Metal Addition

In order to confirm the activity of the KADPE according to the addition of a metal, the enzyme activity was measured under the reaction conditions as in Example 3-1 by replacing MnSO$_4$ with each of various metal salts (LiCl, Na$_2$SO$_4$, MgCl$_2$, NaCl, FeSO$_4$, and MgSO$_4$) and adding each of the metal salts to a final concentration of 3 mM. The control group was not treated with a metal salt.

As a result, it was confirmed that the activity of the KADPE was increased when not only Mn but also Li, Na, Mg, and Fe were added, and that among these, Mn increased the enzyme activity the most (Table 4 and FIG. 5).

TABLE 4

| Metal salt | Relative conversion rate (%) |
|---|---|
| LiCl | 55 |
| Na$_2$SO$_4$ | 57 |
| MgCl$_2$ | 59 |
| NaCl | 54 |
| FeSO$_4$ | 80 |
| MgSO$_4$ | 53 |
| MnSO$_4$ | 100 |
| no metal | 47 |

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

[Accession Number]

Name of Depositary Agency: Korean Culture Center of Microorganisms

Deposition Number: KCCM11917P

Date of Deposition: Oct. 20, 2016

The invention claimed is:

1. A method for producing D-psicose, comprising reacting D-fructose with D-psicose 3-epimerase consisting of the amino acid sequence of SEQ ID NO: 1, a microorganism expressing the D-psicose 3-epimerase, or a culture of the microorganism.

2. The method of claim 1, wherein the D-psicose 3-epimerase is encoded by the polynucleotide sequence of SEQ ID NO: 2.

3. The method of claim 1, wherein the reaction is carried out at a pH of 5.0 to 9.0.

4. The method of claim 1, wherein the reaction is carried out at a temperature of 40° C. to 90° C.

5. The method of claim 1, wherein the reaction is carried out for 0.5 hours to 48 hours.

6. The method of claim 1, wherein the method further comprises reacting a metal with the D-psicose 3-epimerase, the microorganism expressing the D-psicose 3-epimerase, or the culture of the microorganism, before reacting the D-fructose.

7. The method of claim 1, wherein the method further comprises reacting a metal with the D-psicose 3-epimerase, the microorganism expressing the D-psicose 3-epimerase, or the culture of the microorganism, after reacting the D-fructose.

8. The method of claim 1, wherein the method further comprises reacting a metal with the D-psicose 3-epimerase, the microorganism expressing the D-psicose 3-epimerase, or the culture of the microorganism, simultaneously with reacting the D-fructose.

9. A method for producing D-psicose, the D-fructose is reacted with the D-psicose 3-epimerase consisting of the amino acid sequence of SEQ ID NO: 1.

10. The method of claim 1, wherein the method comprises reacting the D-fructose with the microorganism expressing the D-psicose 3-epimerase.

11. The method of claim 1, wherein the method comprises reacting the D-fructose with the culture of the microorganism.

12. The method of claim 6, wherein the metal comprises one or more metals selected from the group consisting of manganese, magnesium, iron, lithium, and sodium.

13. The method of claim 7, wherein the metal comprises one or more metals selected from the group consisting of manganese, magnesium, iron, lithium, and sodium.

14. The method of claim 8, wherein the metal comprises one or more metals selected from the group consisting of manganese, magnesium, iron, lithium, and sodium.

15. The method of claim 1, wherein the reaction is carried out at a pH of 6.0 to 8.5.

16. The method of claim 1, wherein the reaction is carried out at a temperature of 50° C. to 65° C.

17. The method of claim 1, wherein the reaction is carried out for 0.5 hours to 9 hours.

* * * * *

SEQUENCE LISTING

<160> NUMBER OF SEQ ID NOS: 5

<210> SEQ ID NO 1
<211> LENGTH: 297
<212> TYPE: PRT
<213> ORGANISM: Artificial Sequence
<220> FEATURE:
<223> OTHER INFORMATION: Amino acid sequences of KADPE

<400> SEQUENCE: 1

```
Met Lys Asn Lys Leu Gly Val His Ala Gln Val Trp Val Gly Gly Trp
1               5                   10                  15

Ser His Gly Glu Ala Glu Arg Ala Ile Ala Ser Thr Ala Ser Leu Gly
            20                  25                  30

Tyr Asp Tyr Ile Glu Ala Pro Ala Leu Asp Pro Ser Arg Ile Asp Ile
        35                  40                  45

Pro Phe Thr Val Lys Ala Leu Glu Lys His Gly Ile Gly Ile Thr Thr
    50                  55                  60

Ser Leu Gly Leu Asp Asp Ser Cys Asp Ile Ser Ser Gly Asp Ala Asp
65                  70                  75                  80

Lys Lys Ala Arg Gly Glu Ala Gln Leu Met Lys Val Val Ser Thr Thr
                85                  90                  95

Arg Asp Leu Gly Gly Thr His Ile Thr Gly Ile Leu Tyr Ser Gly Phe
            100                 105                 110

Gln Lys Tyr Phe Thr Pro Ala Thr Pro Asp Gly Val Ala Gly Ala Val
        115                 120                 125

Glu Val Leu Arg Arg Val Ala Glu Glu Ala Ala Lys Ser Asn Ile Thr
    130                 135                 140

Leu Gly Leu Glu Val Val Asn Arg Tyr Glu Thr Asn Val Ile Asn Thr
145                 150                 155                 160

Ala Ala Gln Gly Val Glu Leu Cys Lys Arg Val Gly Met Pro Asn Val
                165                 170                 175

Lys Val His Leu Asp Cys Tyr His Met Asn Ile Glu Glu Ala Asp Ala
```

```
                 180                 185                 190
Glu Arg Ala Ile Ile Glu Thr Gly Asp Tyr Leu Gly Tyr Phe His Thr
                195                 200                 205

Gly Glu Ser His Arg Gly Tyr Leu Gly Thr Gly Ser Ile Asp Phe Thr
    210                 215                 220

Lys Ile Phe Arg Gly Leu Val Lys Ala Asn Tyr Gln Gly Pro Ile Cys
225                 230                 235                 240

Phe Glu Ser Phe Ser Ser Ala Val Ala Gly Glu Pro Leu Ser Gly Ile
                245                 250                 255

Leu Gly Ile Trp Arg Asn Leu Trp Thr Asp Ser Thr Asp Leu Cys Arg
            260                 265                 270

His Ala Met Gln Phe Thr Gln Ala Gln Met Lys Ala Ala Glu Glu Ala
        275                 280                 285

Gln Ala Ile Arg Thr Gly Ala Asp Trp
    290                 295

<210> SEQ ID NO 2
<211> LENGTH: 894
<212> TYPE: DNA
<213> ORGANISM: Artificial Sequence
<220> FEATURE:
<223> OTHER INFORMATION: Nucleotide sequences of KADPE

<400> SEQUENCE: 2
atgaagaaca agctcggcgt ccacgcgcag gtctgggtcg gcggctggag ccatggcgag      60
gcggagcgcg ccatcgccag caccgcgtcg ctcggctacg actacatcga ggctccggcc     120
ctcgatccgt cgcggatcga catcccgttc acggtgaagg cgctggaaaa gcacggcatc     180
ggcatcacga cgtcgctcgg cctcgacgac agctgcgaca tctcctcggg cgacgccgac     240
aagaaggcgc gcggcgaggc gcagctgatg aaggtggtct cgacgacgcg cgacctcggc     300
ggcacccaca tcaccggcat cctctattcc ggcttccaga aatactttac gccagccacg     360
cccgacggcg tcgccggcgc cgtcgaggtg ctgcggcggg tggcggagga agccgccaag     420
agcaacatca cgctcggcct tgaggtggtg aaccgctacg agacaaacgt catcaacacg     480
gccgcccagg gcgtcgagct ctgcaagcgc gtcggcatgc cgaacgtgaa ggtgcacctc     540
gactgctacc acatgaacat cgaggaagcc gacgccgagc gcgccatcat cgagaccggc     600
gactatctcg gctacttcca caccggtgaa tcgcaccgcg gctatctcgg caccggctcg     660
atcgacttca cgaagatctt ccgcggcctg gtcaaggcca actaccaagg cccgatctgc     720
ttcgaatcct tctcctccgc cgtcgccggc gagccgcttt ccggcattct cggcatctgg     780
cgcaatctct ggacggattc gaccgatctc tgccgccacg ccatgcagtt cacgcaggcg     840
cagatgaagg cggccgagga agcccaggcg atccgcaccg cgccgactg gtag           894

<210> SEQ ID NO 3
<211> LENGTH: 20
<212> TYPE: DNA
<213> ORGANISM: Artificial Sequence
<220> FEATURE:
<223> OTHER INFORMATION: A forward primer of KADPE

<400> SEQUENCE: 3
atgaagaaca agctcggcgt                                                  20

<210> SEQ ID NO 4
<211> LENGTH: 18
<212> TYPE: DNA
```

<213> ORGANISM: Artificial Sequence
<220> FEATURE:
<223> OTHER INFORMATION: A reverse primer of KADPE

<400> SEQUENCE: 4
ctaccagtcg gcgccggt                                                   18

<210> SEQ ID NO 5
<211> LENGTH: 289
<212> TYPE: PRT
<213> ORGANISM: Artificial Sequence
<220> FEATURE:
<223> OTHER INFORMATION: Amino acid sequences of ATPE

<400> SEQUENCE: 5

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Leu Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly